(12) United States Patent
Hyde et al.

(10) Patent No.: US 10,456,241 B2
(45) Date of Patent: Oct. 29, 2019

(54) SWITCHABLE LENS DEVICES, SYSTEMS, AND RELATED METHODS

(71) Applicant: Elwha LLC, Bellevue, WA (US)

(72) Inventors: Roderick A. Hyde, Redmond, WA (US); Jordin T. Kare, San Jose, CA (US); John Marshall, Farnborough (GB); Clarence T. Tegreene, Mercer Island, WA (US); Roberto Zaldivar, Mendoza (AR); Roger Zaldivar, Mendoza (AR)

(73) Assignee: ELWHA LLC, Bellevue, WA (US)

( * ) Notice: Subject to any disclaimer, the term of this patent is extended or adjusted under 35 U.S.C. 154(b) by 176 days.

(21) Appl. No.: 15/298,945

(22) Filed: Oct. 20, 2016

(65) Prior Publication Data

US 2018/0110614 A1 Apr. 26, 2018

(51) Int. Cl.
*A61F 2/16* (2006.01)
*G02C 7/08* (2006.01)
*G02C 7/10* (2006.01)

(52) U.S. Cl.
CPC ............ *A61F 2/1624* (2013.01); *G02C 7/083* (2013.01); *A61F 2230/0006* (2013.01); *A61F 2230/0008* (2013.01); *G02C 7/101* (2013.01)

(58) Field of Classification Search
CPC .......... G02C 7/041; G02C 7/41; G02C 7/081; A61F 2/1624; A61F 2002/1681; A61F 2230/0006; A61F 2230/0008; A61F 2250/0004
See application file for complete search history.

(56) References Cited

U.S. PATENT DOCUMENTS

| | | | |
|---|---|---|---|
| 5,108,429 A | 4/1992 | Wiley | |
| 7,457,434 B2 | 11/2008 | Azar | |
| 7,809,417 B2 | 10/2010 | Abreu | |
| 8,043,370 B2 * | 10/2011 | Bretthauer | A61B 3/113 623/6.11 |
| 8,919,953 B1 * | 12/2014 | Ho | G02C 7/049 351/159.03 |
| 9,161,113 B1 | 10/2015 | Fenton et al. | |
| 9,877,824 B2 | 1/2018 | Hyde et al. | |
| 2007/0016074 A1 | 1/2007 | Abreu | |
| 2012/0165597 A1 | 6/2012 | Proulx et al. | |
| 2013/0282117 A1 | 10/2013 | Van Heugten et al. | |
| 2015/0185503 A1 * | 7/2015 | Tate | G06F 3/013 351/158 |
| 2015/0366656 A1 | 12/2015 | Wortz et al. | |
| 2015/0366659 A1 | 12/2015 | Wortz et al. | |
| 2016/0033793 A1 | 2/2016 | Fenton et al. | |
| 2016/0062150 A1 | 3/2016 | Sako et al. | |
| 2016/0166200 A1 | 6/2016 | Bal | |
| 2017/0023801 A1 | 1/2017 | Hyde et al. | |

OTHER PUBLICATIONS

PCT International Search Report; International App. No. PCT/US2017/057108; dated Jan. 17, 2018; pp. 1-3.

\* cited by examiner

*Primary Examiner* — David H Willse
*Assistant Examiner* — Tiffany P Shipmon
(74) *Attorney, Agent, or Firm* — Dorsey & Whitney LLP (57) ABSTRACT

Embodiments disclosed herein are directed to switchable lens devices, systems, and methods related to detecting one or more commands and switching one or more switchable lenses responsive to one or more detected commands.

44 Claims, 7 Drawing Sheets

SWITCHABLE LENS DEVICES, SYSTEMS, AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Intraocular lenses (IOLs), such as pseudophakic IOLs, aphikic IOLs, or phakic IOLs (PIOLS), can be used to correct the vision of a subject. Typical IOLs can include monofocal, multifocal, or accommodative configurations. IOLs can include an optic element (e.g., lens) and haptic elements (e.g., arms or wings configured to aid in positioning the IOL).

Such configurations can be limited to focusing either on near or far vision without selectively modifiable adjustment therebetween. Therefore, manufacturers, users, and designers of IOLs continue to seek improved IOLs.

SUMMARY

Embodiments disclosed herein are directed to switchable lens devices and systems, such as IOL devices and IOL systems, and methods that include controlling the switching of the switchable lenses. For example, as described below in more detail, the switchable lenses can have multiple optical settings and can be switched from one optical setting to another (e.g., responsive to one or more switching signals from a controller). In an embodiment, the controller can receive one or more inputs from a user and can switch or direct switching of one or more switchable lenses.

An embodiment includes a lens system that includes at least one switchable lens device sized and configured to be placed in association with at least one of a first eye of the subject or a second eye of the subject. The at least one switchable lens device includes at least one switchable lens that has a plurality of optical settings and is configured to selectively switch at least between a first optical setting of the plurality of optical settings and a second optical setting of the plurality of optical settings. Also, the first optical setting includes at least one of a first focal spot or a first visible-light-transmittance setting of the at least one switchable lens, and the second optical setting includes at least one of a second focal spot or a second visible-light-transmittance setting of the at least one switchable lens. The lens system also includes a controller operably coupled to the at least one switchable lens device. The controller includes control electrical circuitry configured to receive one or more audible inputs from the subject and to correlate the one or more received inputs with the first optical setting of the plurality of optical settings. Moreover, the controller is configured to direct switching of the at least one switchable lens from the first optical setting of the plurality of optical settings to the second optical setting of the plurality of optical settings.

An embodiment includes a lens system that includes at least one switchable lens device sized and configured to be placed in association with at least one of a first eye of the subject or a second eye of the subject. The at least one switchable lens device includes at least one switchable lens that has a plurality of optical settings and being configured to selectively switch at least between a first optical setting of the plurality of optical settings and a second optical setting of the plurality of optical settings. The first optical setting includes at least one of a first focal spot or a first visible-light-transmittance setting of the at least one switchable lens. The second optical setting includes at least one of a second focal spot or a second visible-light-transmittance setting of the at least one switchable lens. The lens system also includes a controller operably coupled to the at least one switchable lens device, the controller including control electrical circuitry configured to receive one or more selected gesture inputs from the subject and to correlate the one or more received inputs with the first optical setting of the plurality of optical settings. The controller is also configured to direct switching of the at least one switchable lens from the first optical setting of the plurality of optical settings to the second optical setting of the plurality of optical settings.

An embodiment includes a method of selectively modifying an optical setting of at least one switchable lens placed in a first eye or a second eye of a subject. The method includes, at a controller, receiving one or more audible inputs from the subject, and generating a switching output for switching the at least one switchable lens of at least one switchable lens device from a first optical setting to a second optical setting responsive to the one or more audible inputs received from the subject. The first optical setting includes at least one of a first focal spot or a first visible-light-transmittance setting of the at least one switchable lens. The second optical setting includes at least one of a second focal spot or a second visible-light-transmittance setting of the at least one switchable lens. The method also includes switching the at least one switchable lens from the first optical setting to the second optical setting responsive at least partially to the generated switching output.

An embodiment includes a method of selectively modifying an optical setting of at least one switchable lens placed in a first eye or a second eye of a subject. The method includes, at a controller, receiving one or more gesture inputs from the subject, and generating a switching output for switching the at least one switchable lens of at least one switchable lens device from a first optical setting to a second optical setting responsive to the one or more gesture inputs received from the subject. The first optical setting includes at least one of a first focal spot or a first visible-light-transmittance setting of the at least one switchable lens. The second optical setting includes at least one of a second focal spot or a second visible-light-transmittance setting of the at least one switchable lens. The method also includes switching the at least one switchable lens from the first optical setting to the second optical setting responsive at least partially to the generated switching output.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Embodiments disclosed herein are directed to switchable lens devices and systems, such as IOL devices and IOL systems, and methods that include controlling the switching of the switchable lenses. For example, as described below in more detail, the switchable lenses can have multiple optical settings and can be switched from one optical setting to another (e.g., responsive to one or more switching signals from a controller). In an embodiment, the controller can receive one or more inputs from a user and can switch or direct switching of one or more switchable lenses.

For example, the controller can include or can be operably coupled to one or more input devices or sensors that can detect or receive input (e.g., input provided by a user or subject wearing or using the lens device or system). In an embodiment, the controller can be operably coupled to an audio detection device, such as a microphone (e.g., piezo microphone, laser microphone, condenser microphone, etc.). Hence, for example, the controller can receive one or more audible inputs and can correlate the audible inputs to one or more optical settings for the switchable lens(es) or to one or more switching commands. The controller can switch or direct switching of one or more switchable lenses responsive to the switching commands (e.g., switching command can be correlated to a specific optical setting for one or more of the switchable lenses).

In one or more embodiments, the controller can include or can be operably coupled to one or more motion or gesture detection sensors. For example, the sensors can detect one or more selected movements or gestures (e.g., gestures made by the subject). The controller can receive one or more signals from the motion or gesture detection sensors and can correlate subject's gestures or movements with one or more switching commands. For example, responsive to one or more switching commands received from the subject, the controller can change one or more optical settings of one or more of the switchable lenses, as described herein.

In an embodiment, the switchable lens systems disclosed herein can include one or more sensors configured to detect one or more physiological indicia of the subject. For example, the switchable lens system can include one or more sensors configured to detect glucose concentration (e.g., in the eye of the subject), eye pressure, heart rate, biological proteins present in the eye, or any other biological indicia. The one or more sensors can be operably coupled to the controller. The controller of the switchable lens system can be configured to transmit the measurements of the physical indicia to a remote source such as a computer, a cellular phone, or other electronic device. In an embodiment, the measured physical indicia may be used to determine the health of a subject or eye thereof, customize the operation of the switchable lens device to the particular subject, determine if the controller needs to be removed or adjusted, or determine if the focal adjustments of the controller are suitable for the subject. The electronic device may then transmit instructions to the controller to selectively control or otherwise adjust the functioning of the switchable lens system, such as controllably changing the focal length of the switchable lens device.

Figure 1:
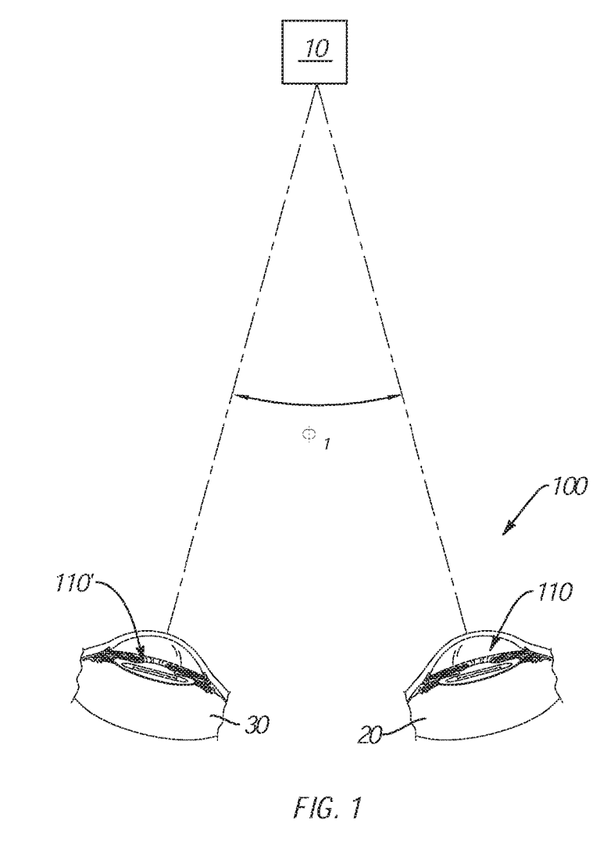
FIG. 1 is a schematic top view of a subject's eyes having a first vergence therebetween and focused on a first object at a first distance from the subject, according to an embodiment.

In an embodiment, the switchable lens can be configured to switch between two or more focal lengths. FIG. 1 schematically illustrates eyes 20 and 30 of a subject focused on a first object 10 that is positioned at a first distance from the subject. In particular, when the eyes 20, 30 are focused on the first object 10, an angle between respective optical axes thereof can be at a vergence angle $\phi_1$. FIG. 1 also schematically illustrates a switchable lens system 100, according to an embodiment. For example, switchable lens system 100 can include a first switchable lens device 110 positioned in a first eye 20 and a second switchable lens device 110' positioned in a second eye 30 of the subject.

Generally, the first switchable lens device 110 or the second switchable lens device 110' can be configured to augment or correct visual deficiencies of the subject or to replace the lenses in the respective first eye 20 or second eye 30 of the subject (e.g., in cataract surgeries). It should be appreciated that, in one or more embodiments, the switchable lens system 100 can include only a single switchable lens device (e.g., the first switchable lens device 110 or the second switchable lens device 110'), which can be associated with or positioned in the first eye 20 or in the second eye 30. The switchable lens devices 110 or 110' can be switched to or set at a first optical setting, such as a first focal length.

Figure 2:
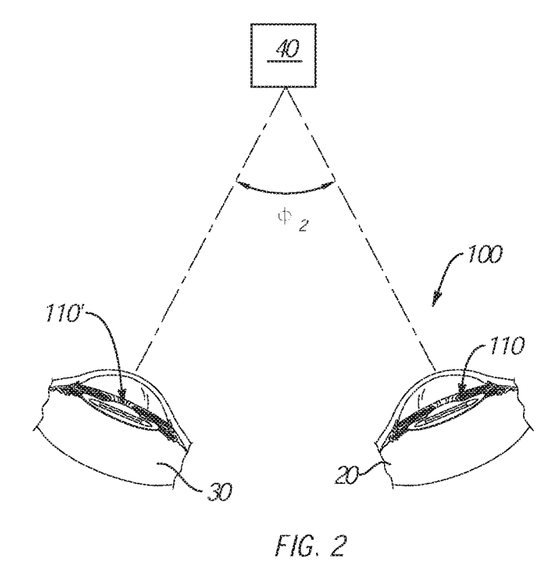
FIG. 2 is a schematic top view of the subject's eyes of FIG. 1, with the eyes having a second vergence therebetween and are focused on a second object at a second distance from the subject that is less than the first distance, according to an embodiment.

For example, at the first focal length, the light entering the eye from the distance of the first object 10 is focused on the retina of the respective eyes 20, 30, thereby focusing the eyes 20, 30 on the first object 10. Moreover, the switchable lens devices 110 or 110' can be switched to a second optical setting, such as a second focal length. When the subject focuses on another object, such as an object that is closer to the subject than the first object 10, the subject's eyes 20, 30 can tilt such as to converge, thereby changing the angle between the optical axes thereof. FIG. 2 schematically shows the subject's eyes 20, 30 focused on a second object 40, which is positioned at a second distance and closer to the subject than the first object 10 (FIG. 1). For example, when the eyes 20, 30 focus on the second object 40, the angle between the optical axes thereof can change to a second angle $\phi_2$. More specifically, as the eyes 20, 30 focus on the closer, second object 40, the eyes 20, 30 converge or in-tilt, such that the second angle $\phi_2$ defined by the respective optical axis thereof is greater than the first angle $\phi_1$.

In an embodiment, the switchable lens devices 110 or 110' can be switched to the second focal length, which can be shorter than the first focal length. The switchable lens devices 110 or 110' can include one or more sensors that can sense or detect a one or more instructions or inputs (e.g., one or more inputs from the subject) and can correlate the one or more inputs from the subject to a change in vergence rotation between the eyes 20, 30 (e.g., convergence to focus on a closer object or divergence to focus on a farther object) or to a requests or command to change one or more optical settings of the switchable lens devices 110 or 110' (e.g., to change a focal length, to change visible-light transmittance, the change focal spot, etc.).

Generally, switchable lenses can have any number of optical settings, and the controller can directly or indirectly select at least one of the optical settings for the switchable lens. Hence, for example, the switchable lens devices (e.g., the switchable lens device 110 or switchable lens device 110') can be configured for switching among any suitable number of optical settings, as described below in more detail. In one or more embodiments, the switchable lens devices described herein may have optical settings with a single optical parameter (e.g., focal length, light transmittance, etc.) or multiple optical parameters.

Figure 3A:
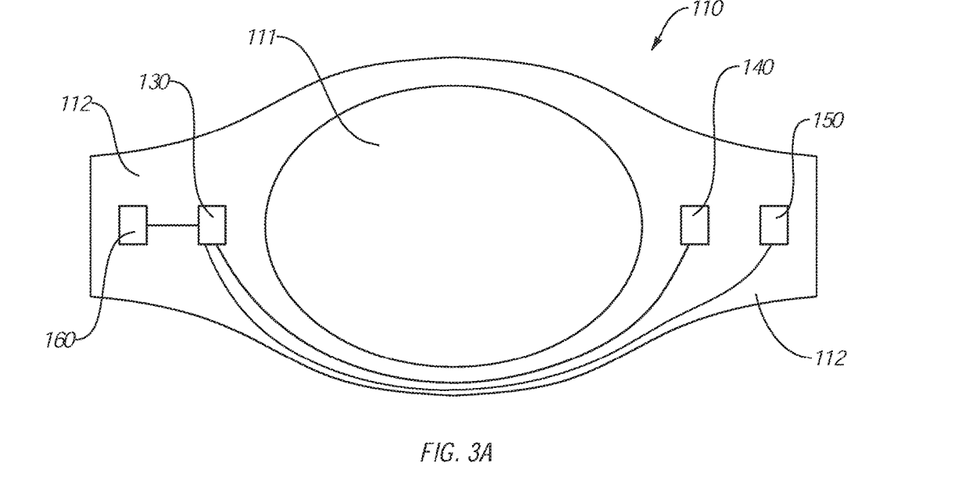
FIG. 3A is a schematic top view of a switchable lens device located in the eye, according to an embodiment.
Figure 3B:
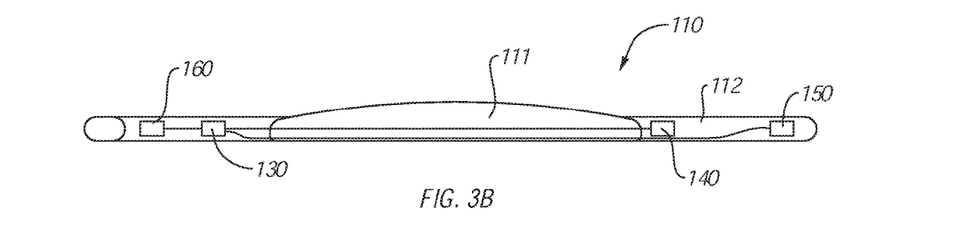
FIG. 3B is a schematic side view of the switchable lens device of FIG. 3A.

FIGS. 3A and 3B illustrate the switchable lens device 110, according to an embodiment. FIG. 3A is a top view of the switchable lens device 110 and FIG. 3B is a side view of the switchable lens device 110. It should be appreciated, however, that the switchable lens 110' (FIGS. 1A-1B) can be similar to or the same as the switchable lens device 110. Generally, the switchable lens device 110 can include a switchable lens 111 and haptics 112 connected to or integrated with the switchable lens 111. In an embodiment, the haptics 112 can be positioned on or secured to one or more structures in the eye, thereby positioning or securing the switchable lens device 110 in the eye.

For example, the haptics 112 can be positioned on the ciliary body or muscles or in or on the capsular bag of the natural lens of the eye. The switchable lens 111 can be located laterally in the center of the eye with the haptics 112 extending laterally therefrom. As mentioned above, the switchable lens 111 of the switchable lens device 110 can be switched between two or more optical setting (e.g., two or more focal lengths, to focus light entering the eye from a selected distance on the retina of the eye), thereby augmenting or correcting the vision of the subject.

In an embodiment, the switchable lens device 110 can be substantially fixed within the eye (e.g., switchable lens device can be substantially immobile relative to the optical axis of the eye). As such, for example, movement of the eye 20 can result in a corresponding movement of the switchable lens device 110. In particular, as the eye 20 tilts or pivots in the eye socket, the switchable lens device 110 can correspondingly tilt or pivot together with the eye. Furthermore, one, some, or all of the elements or components of the switchable lens device 110 can have a predetermined orientation relative to the eye or relative to the optical axis thereof, as described below in more detail.

In an embodiment, a controller including control electrical circuitry can be operably coupled to the switchable lens 111 and can switch or direct switching of the switchable lens 111 between two or more optical settings (e.g., between two or more focal lengths). In an embodiment, the controller can be positioned on or embedded in one or more portions of the switchable lens device 110. For example, a controller 130 can be mounted on, embedded in, or otherwise mechanically connected to the haptics 112 (e.g., as schematically shown in FIG. 3B). Additionally or alternatively, the controller 130 can be mounted on, embedded in, or otherwise mechanically connected to the switchable lens 111 or any other suitable portion of the switchable lens device 110.

In an embodiment, the controller 130 can receive a detection output from an input sensor. For example, the detection output can be related or can correspond to one or more commands or selections for one or more optical settings (e.g., for a single optical setting for one or more switchable lenses or for multiple optical settings for two or more switchable lenses). At least partially based on the received detection output, the controller 130 can switch the switchable lens 111 to a selected or predetermined optical setting.

In an embodiment, the switchable lens device 110 can be configured to switch between two or more discrete optical settings. For example, the switchable lens device 110 can have set or specific focal lengths to which the switchable lens 111 can be switched (e.g., a first focal length for viewing nearby object and a second focal length for viewing objects at a distance). Similarly, the switchable lens device 110 can be switched between two or more discrete settings for the visible-light transmittance through the switchable lens 111.

In an embodiment, the switchable lens device 110 includes an input sensor 140. The controller 130 can receive one or more signals from the input sensor 140 and, responsive thereto, can select or switch the switchable lens 111 to a selected optical setting. For example, the controller 130 can switch or direct switching of the switchable lens 111 from a first focal length to a second focal length. In an embodiment, at the first focal length, the switchable lens 111 can have a different focal or optical power than at the second focal length.

In an embodiment, the input sensor 140 can detect one or more inputs that can be correlated to a selection of at least one optical setting for the switchable lens 111. For example, as described below in more detail, responsive to the signal(s) received from the input sensor 140, the controller 130 can switch or direct switching of the switchable lens 111 to a selected optical settings (e.g., the controller 130 can generate one or more switching signals that can be based on or responsive to the signal(s) received from the input sensor 140).

In an embodiment, the input sensor 140 can include one or more audio or sounds sensors or detectors (e.g., a microphone). For example, the input sensor 140 can detect an audio input or command, and the controller 130 can receive one or more signals from the input sensor 140, which can correspond to the audio input(s) detected by the input sensor 140. Moreover, the controller 130 can correlate the audio input(s) detected by the input sensor 140 or the signals received from the input sensor 140 to one or more switching commands or to one or more optical settings for the switchable lens 111.

For example, the subject wearing or using the switchable lens device 110 can provide an audible command requesting that the switchable lens device 110 switch the switchable lens 111 from a first optical setting to a second optical setting, or vice versa. The input sensor 140 can detect the audible command provided by the subject, and responsive to the detection of the audible command at the input sensor 140, the controller 130 can receive one or more signals from the input sensor 140. Moreover, as discussed above, the controller 130 can correlate the one or more signals received from the input sensor 140 to one or more optical settings corresponding thereto and requested by the subject. Responsive to the audible command (e.g., from the subject), the controller 130 also can switch the switchable lens 111 from the first optical setting to the second optical setting, from the second optical setting to a third optical setting, and so on, by switching or directing the switching of the switchable lens 111 to the optical setting that corresponds to the command detected by the input sensor 140.

In an embodiment, the controller 130 can correlate an audible command or input (e.g., from the subject) with an optical setting for the switchable lens 111. For example, an audible command can be a voice command. Hence, in an embodiment, the controller 130 can correlate verbal audible commands or sounds, such as subject speaking out loud a phrase, a number, a parameter, etc., with a selected optical setting. In an embodiment, the controller 130 can be programmed or configured to filter out voice commands from persons other than the subject. For example, the controller 130 can be configured or programmed to distinguish the voice of the subject from persons other than the subject.

Additionally or alternatively, audible commands can include non-verbal commands. Generally, the non-verbal commands can include any suitable or repeatable sound or noise that can be associated with a specific optical setting for the switchable lens 111. For example, suitable non-verbal commands can include clacking of teeth, clapping, clicking, etc. The controller 130 can be configured to correlate non-verbal commands to specific or corresponding optical settings. For example, the subject can train the controller 130 to correlate a clicking sound with a first optical setting, and clacking of teeth with a second optical setting.

In an embodiment, a command for switching the switchable lens 111 to a suitable or selected optical setting can involve a series, a sequence, or a pattern of non-verbal commands or sounds. For example, a selected number of repeated claps, clicks, combinations thereof, etc., can be correlated with a selection for a specific optical setting. In an embodiment, the selected number of non-verbal or repeated commands must be provided by the subject within a selected time period. For example, the controller 130 can filter out verbal or non-verbal inputs (or signals received from the input sensor 140, which correspond to the verbal and non-verbal inputs) that do not correspond to a command input (e.g., verbal or non-verbal inputs that do not include or correspond to a selected sound, selected number of repeats of the sound(s), time period within which the sound(s) were repeated, etc.). Hence, for example, the controller 130 can filter out signals received from the input sensor 140, which do not correspond to a command for switching the switchable lens 111 from one optical setting to another. It should be appreciated that, as described below in more detail, the switchable lens device 110 can include any number of suitable sensors or detectors that can detect any number of inputs (e.g., inputs from the subject using the switchable lens device 110); the sensors or detectors can generate one or more signals responsive to such inputs, and the signals can be correlated by the controller 130 to one or more optical settings.

As mentioned above, the optical settings for the switchable lens 111 of the switchable lens device 110 can involve any number of suitable optical properties. For example, the switchable lens 111 can be switchable between two or more focal lengths. In an embodiment, the switchable lens 111 can be configured to switch between at least two different optical settings (e.g., between two different focal lengths) responsive to one or more electrical inputs. Hence, for example, the controller 130 can switch or direct switching of the switchable lens 111 between two or more optical settings by generating a suitable electrical signal. That is, the switchable lens 111 can be an electrically-modifiable diffractive lens, such as the electrically-modifiable lenses described in more detail in U.S. application Ser. No. 14/807,673, the entire content of which is incorporated herein by this reference. Additionally or alternatively, the switchable lens 111 can be liquid crystal lens (e.g., a liquid crystal lens with an electrically tunable focal length).

In an embodiment, the switchable lens 111 can be configured to focus light on two or more different locations of the subject's retina. For example, the switchable lens 111 can be movable relative to the haptics 112. For example, the switchable lens 111 can focus the light on a first location of the subject's retina when the switchable lens 111 is at a first location or at a first orientation relative to the haptics 112, and can focus light on the second location of the subject's retina, when the switchable lens 111 is at a second location or a second orientation relative to the haptics 112. Hence, for example, a subject with a macular degeneration condition (e.g., age-related macular degeneration) can have the switchable lens 111 focus light on one or more portions of the retina that are suitably healthy, such as to facilitate improvement or at least partial restoration of the subject's vision.

For example, the controller 130 can switch or direct switching of the switchable lens 111, such that the switchable lens 111 moves relative to the haptics 112 in response to one or more signals received at the controller 130 from the input sensor 140 (e.g., as described above). In an embodiment, the subject can provide a command to the controller 130 (e.g., an audible command or other suitable command, as described below in more detail) to move the switchable lens 111 relative to the haptics 112, such that the light therefrom is focused on a suitable portion of the subject's retina.

Generally, the switchable lens device 110 can include any number of suitable mechanisms that can be configured to reposition or reorient the switchable lens 111 relative to the haptics 112. In an embodiment, the switchable lens device 110 can include one or more shape memory alloys that can move the switchable lens 111 between at least two suitable positions and orientations (e.g., relative to the subject's retina). For example, the switchable lens 111 can be operably coupled to the haptics 112 with one or more connectors including shape memory alloy, such that the switchable lens 111 can be moved relative to the haptics 112 (e.g., the controller 130 can be operably coupled to the shape memory alloy connectors, such that the controller can send or direct sending of a suitable electrical signal to the connectors, which can reconfigure the connectors and move the switchable lens 111 relative to the haptics 112).

In an embodiment, when the switchable lens 111 is on the first optical setting, the switchable lens 111 can be positioned at a first position relative to the haptics 112, when the switchable lens 111 is on the second optical setting, the haptics 112 can be positioned at a second, different position (e.g., laterally different) relative to the haptics 112. For example, the subject can provide a first command to position the switchable lens 111 relative to the haptics 112 at the first position and can provide a second command to position the switchable lens 111 relative to the haptics 112 at the second position. For example, when the switchable lens 111 is in the first position, the switchable lens 111 can focus the light on a first focal spot or location of the subject's retina, and when the switchable lens 111 is in the second position, the switchable lens 111 can focus the light on a second, different focal spot or location of the subject's retina. The first focal spot can be laterally offset from the second focal spot (e.g., the first focal spot can be horizontally or vertically offset relative to the second focal spot). In an embodiment, as described above, the input sensor 140 can detect the audible input; the controller 130 can receive signals from the input sensor 140, which can correspond to the audible input detected by the input sensor 140; responsive to the received signals, the controller 130 can switch or direct switching of the optical setting of the switchable lens 111, such that the switchable lens 111 is positioned at the position that corresponds to the command provided by the subject (e.g., such that the switchable lens 111 moves laterally from the first position to the second position).

It should be appreciated that any optical setting may involve at least one optical parameter, such as focal length, focal or optical power (e.g., magnification), light transmission, focal position, etc. In some embodiments, at least one optical setting includes multiple optical parameters. In an embodiment, the controller 130 can store (directly or indirectly (e.g., the controller 130 can be operably coupled to a storage)) multiple optical settings and corresponding optical parameters thereof. Moreover, the controller 130 can store multiple optical settings and corresponding switching commands (e.g., audible commands or inputs) for switching to each optical setting. For example, the controller 130 can include or can be operably coupled to a table that correlated multiple optical settings with corresponding optical parameters and switching commands (e.g., commands that can be received from the subject) or signals (e.g., signals that can be received from the input sensor 140).

In an embodiment, subject may request the controller 130 to switch the switchable lens 111 to a first optical setting, under which the switchable lens 111 can have a first position relative to the haptics 112, a first focal length, and a first visible-light-transmittance setting. As mentioned above, any number of suitable commands or inputs (e.g., audible input, gesture inputs (described below), etc.) can be provided to the controller 130 (e.g., via the detection at the input sensor 140, which the subject can input the switching command or request to change from one optical setting to another). For example, the subject may speak a phrase (e.g., "first setting") that can be detected by the input sensor 140, and, responsive to the signals received from the input sensor 140, the controller 130 can generate a switching signal, switch, or direct switching of the switchable lens 111 to the selected or corresponding optical setting.

In an embodiment, the switchable lens device 110 can include at least one output device 150. For example, the output device 150 can provide an indication to the subject that the controller 130 received an input from the subject or accepted, or executed a command for switching from one optical setting to another (e.g., a command that corresponds to the input received from the subject). In an embodiment, the controller 130 can be operably coupled to the output device 150 and can send one or more signals thereto, indicating that the controller 130 has received one or more signals from the input sensor 140, which correspond to at least one command for switching the switchable lens 111 from one optical setting to another. For example, responsive to the signal(s) received (directly or indirectly) from the controller 130, the output device 150 can generate an output that is identifiable by the subject.

In an embodiment, the output device 150 can include a speaker that can generate an audible feedback to the subject. For example, the speaker can produce one or more selected non-verbal sounds, such as beeping, clicking, etc., or one or more selected verbal sounds, such as a spoken word or phrase (e.g., "selection accepted"). It should be appreciated, however, that the output device 150 can include any number of output devices suitable for providing feedback to the subject, which is suitably or sufficiently identifiable by the subject.

In an embodiment, the output device 150 can include a haptic feedback generator. For example, the output device 150 can vibrate, pulse, etc., in a manner that can be detected or identified by the subject. Moreover, a selected combination or pattern of haptic feedback can provide the subject with a specific feedback or identification, which can indicate to the subject that the controller 130 received an input from the subject or accepted, or executed a command for switching from one optical setting to another. For example, a short pulse can indicate that the subject's command was accepted by the controller 130, and a longer pulse can indicate that the subject's command was not accepted by the controller 130. Additionally or alternatively, the output device 150 can include a visible indicator. For example, the output device 150 can include a visible indicator. For example, the visible indicator can include lights of one or more selected wavelengths. In an embodiment, the light(s) can be produced by a light generator (e.g., LED) that can generate feedback of suitable color, intensity, pattern (e.g., Morse code), etc., to provide suitable feedback to the subject.

In an embodiment, the switchable lens device 110 can include a communication device 160 (e.g., the controller 130 can be operably coupled to the communication device 160). The communication device 160 can be mounted on or embedded in one or more portions of the switchable lens device 110. For example, the communication device 160 can be embedded in or mechanically connected to the haptics 112 or the switchable lens 111 of the switchable lens device 110.

In an embodiment, the communication device 160 can be wireless (e.g., the communication device 160 can be a transmitter or a transceiver) or wired. For example, a wireless (e.g., RF-based or US-based) connection can be established between the communication device 160 and another or additional communication device. Alternatively, the communication device 160 and another communication device can have a wired connection therebetween. For example, an electrical conductor connecting the communication device 160 and another communication device can be implanted in or near the eyes of the subject. In any embodiment, the communication device 160 can be operably coupled to the additional communication device, such as to send data therebetween.

In an embodiment, the controller 130, input sensor 140, output device 150, or communication device 160 can be operably coupled or connected to a power source. For example, the power source can include a rechargeable energy storage device or battery (not shown) that can be mounted on or embedded in the switchable lens device 110. The battery can be wirelessly recharged (e.g., a wireless or inductive charger can recharge the battery). In an embodiment, the battery can be operably connected to a photovoltaic cell that can be mounted on or embedded in the switchable lens device 110. Alternatively or additionally, the battery can be operably connected or coupled to a charge port that can be configured to accept a charging device. In any event, the power source can power one or more of the controller 130, input sensor 140, output device 150, or communication device 160.

In an embodiment, the power source may include a parasitic power device, such as an induction coil, one or more photocells, thermoelectric device, or any other device configured to harvest energy from a subject or the environment. For example, the induction coil can include a channel having a magnet therein, the channel passing the induction coil upon movement of the subject (e.g., eye-movement or blinking). In an embodiment, an induction coil can be disposed in the eye of a subject (e.g., in or adjacent to the switchable lens) and a corresponding magnet may be positioned on an adjacent part of the subject (e.g., an eyelid or bridge of the nose) whereby movement of the eye or eyelid can cause a current in the induction coil.

As described above, the switchable lens system can include a single switchable lens device or multiple switchable lens devices (e.g., a switchable lens device can be located in one or in both eyes of the subject). Generally, the switchable lens devices of the switchable lens system can be similar to or the same as the switchable lens device 110. It should be appreciated, however, that any of the switchable lens devices included in the switchable lens systems described herein can include or can be operably coupled to any number of controllers, input sensors, output devices, or combinations thereof, which can be similar to or the same as the controller 130, input sensor 140, output device 150, and communication device 160.

While the switchable lens device 110 is described as including the controller 130, input sensor 140, output device 150, and communication device 160, configurations of the switchable lens device 110 can vary from one embodiment to the next. For example, the switchable lens device 110 can include the switchable lens 111, and the controller 130, input sensor 140, or output device 150 can be positioned externally to the switchable lens device 110. For example, the controller 130, input sensor 140, or output device 150 can be included in an external device, such as a personal electronic device (e.g., subject's smart phone). Moreover, as described above, the subject can wear switchable lens devices in both eyes. Hence, for example, a first switchable lens device can include the switchable lens 111, controller 130, input sensor 140, output device 150, communication device 160, or any combination thereof, while the second switchable lens device can include a switchable lens and a communication devices operably coupled to the communication device 160 and configured received switching signals therefrom (e.g., the controller 130 can generate switching signals or direct switching of the switchable lens 111 and of a second switchable lens).

In the illustrated embodiment, the switchable lens 111 is an intraocular lens. It should be appreciated, however, that the switchable lens 111 can be any other suitable lens, as described below in more detail. For example, the switchable lens can be included in or can form a part of a contact lens that can be worn by the subject. Additionally or alternatively, the switchable lens can be included in one or more devices positionable externally to the subject's eye. As described below in more detail, for example, the switchable lenses can be included in spectacles, goggles, shields, etc.

Moreover, the input sensor 140 can include any number of sensors suitable for detecting subject's input. For example, as described below in more detail, the input sensor 140 can include one or more motion sensors (e.g., accelerometers) that can detect movements or gestures of the subject (e.g., movements of subject's head) that can be made by the subject as an input of a command to the controller 130. In an embodiment, the controller 130 can correlate one or more signals received from accelerometer(s) to one or more commands for switching the switchable lens 111 (e.g., as described above in connection with audible commands). For example, a sequence of nods, turns, etc., of subject's head can be detected by the input sensor 140, and responsive to such detection, the controller 130 can switch the switchable lens 111 to a corresponding optical setting.

Moreover, the controller 130 can receive a one or more inputs from one or more sensors configured to detect one or more physiological characteristics sensor, etc. The detection input(s) from the sensor(s) can be related or correspond to the vergence rotation between the subject's eyes. At least partially based on the received output(s), the controller 130 can switch the lens 111 to a suitable or predetermined focal length. For example, the controller 130 can be operably coupled to and can receive input(s) from the physiological characteristic sensor(s) that can be positioned on or embedded in one or more portions of the switchable lens device 110.

Figure 4:
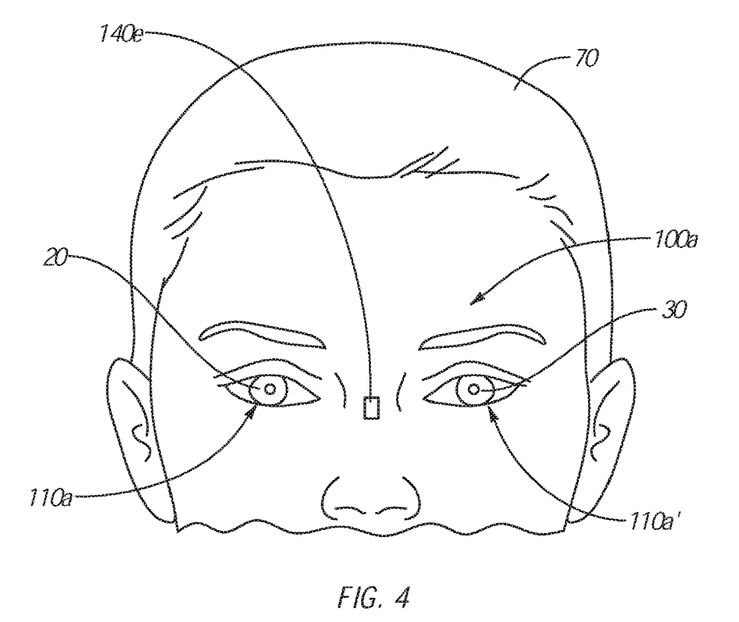
FIG. 4 is a schematic front view of a switchable lens system worn by a subject, according to an embodiment.

In the illustrated embodiment, controller 130 is mechanically coupled or connected to the switchable lens device 110. Similarly, the input sensor 140 and output device 150 are physically positioned on or included in the switchable lens device 110. Again, however, controllers, input sensors, output devices, or combinations thereof, can be positioned remotely of the switchable lens device, at any number of suitable locations or positions. FIG. 4 illustrates a switchable lens system 100a, according to an embodiment. The switchable lens system 100a can include switchable lens device 110a and switchable lens device 110a', which can be positioned in the eyes 20 and 30, respectively, of the subject 70. Except as otherwise described herein, the switchable lens device 110a and switchable lens device 110a' and their respective elements and components can be similar to or the same as any other switchable lens device described herein and their elements and components.

As mentioned above, the switchable lens device 110a or the switchable lens device 110a' can include respective switchable lenses that can be controlled by a single controller or each of which can be controlled by a separate controller. Furthermore, the switchable lens device 110a or the switchable lens device 110a' can include fewer elements or components than the switchable lens device 110 (FIGS. 3A-3B). For example, as shown in FIG. 4, the switchable lens system 100a can include an input sensor 140a that can be positioned externally to the switchable lens device 110a and to the switchable lens device 110a'. In the illustrated embodiment, the input sensor 140a is positioned between the eyes 20, 30 of the subject 70 (e.g., the input sensor 140a can be implanted under the skin of the subject 70).

It should be appreciated that the input sensor 140a can be positioned at any number of suitable locations. Moreover, the input sensor 140a can be operably coupled to one or more controllers of the switchable lens system 100a; the controller(s) can receive one or more signals from the input sensor 140a (e.g., as described above) and can switch or direct switching of the switchable lenses of the switchable lens device 110a or switchable lens device 110a'. Additionally or alternatively, any other element or component of the switchable lens device 110a or switchable lens device 110a' can be positioned externally thereto.

Figure 5:
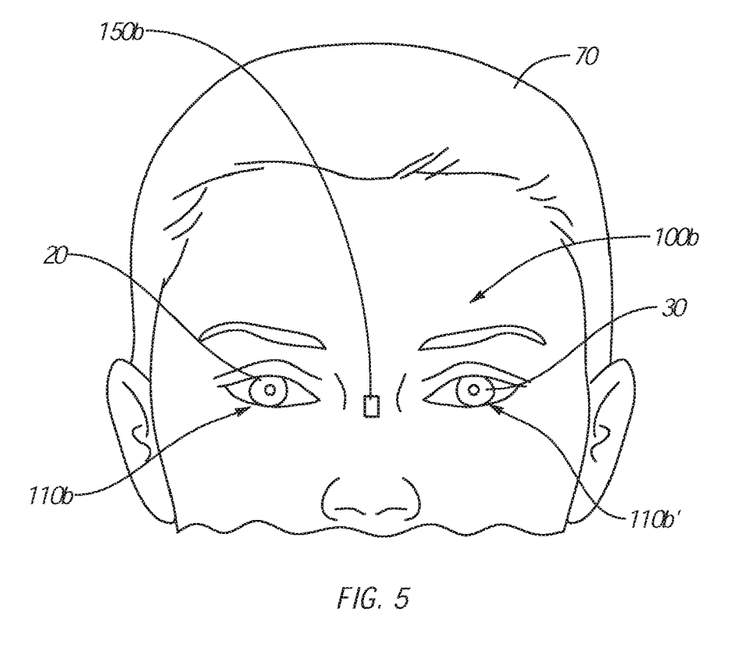
FIG. 5 is a schematic front view of a switchable lens system worn by a subject, according to an embodiment.

FIG. 5 illustrates switchable lens system 100b according to an embodiment. Similar to the switchable lens system 100a (FIG. 4), the switchable lens system 100b can include switchable lens device 110b and switchable lens device 110b', which can be positioned in the eyes 20 and 30, respectively, of the subject 70. Except as otherwise described herein, the switchable lens device 110b and switchable lens device 110b' and their respective elements and components can be similar to or the same as any other switchable lens device described herein and their elements and components.

In the illustrated embodiment, the switchable lens system 100b includes an output device 150b positioned between the eyes 20, 30 of the subject 70. As mentioned above, the output device 150b can provide notification to the subject 70 that the controller has received or accepted a command (e.g., command from the subject 70). For example, the output device 150b can provide haptic feedback to the subject 70, responsive to the controller accepting, rejecting, or executing at least one command from the subject 70. It should be appreciated that the output device 150b can be positioned at any number of suitable locations. Moreover, the output device 150b can be operably coupled to one or more controllers of the switchable lens system 100b; the output device 150b can receive one or more signals from the controller(s) (e.g., as described above) and can provide corresponding feedback to the subject 70.

Figure 6:
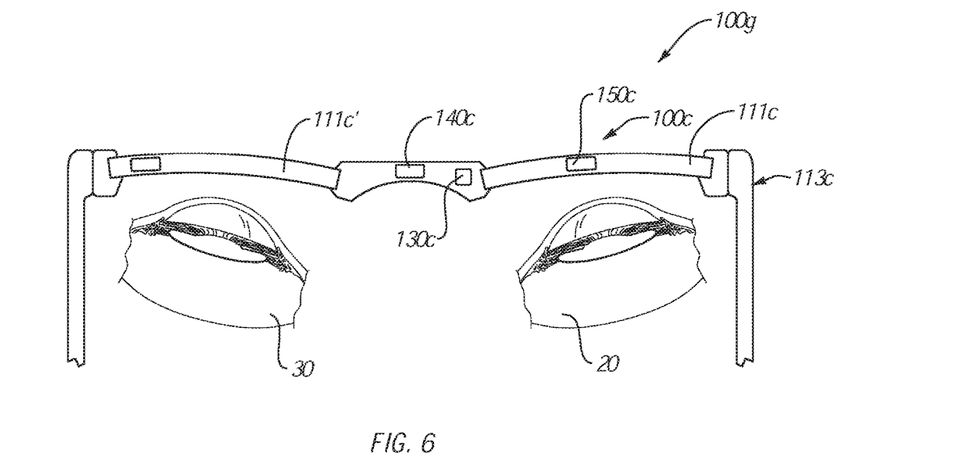
FIG. 6 is a schematic top view of a switchable lens system, according to an embodiment.

As mentioned above, switchable lenses can be included in one or more devices positionable externally to the eyes of the subject. Moreover, any of the elements or components described above in connection with the switchable lens can be included in or mechanically connected to the switchable lens device that is positionable externally to the subject's eyes (e.g., in spectacles). FIG. 6 illustrates a switchable lens system 100c, according to an embodiment. Specifically, the switchable lens system 100c is configured as spectacles. The switchable lens system 100c can include switchable lens device 110c that includes switchable lens 111c and switchable lens 111c' secured in a frame 113c, with the switchable lens 111c and switchable lens 111c' positionable in front of respective eyes 20, 30 of the subject. Except as otherwise described herein, the switchable lens device 110c and its elements and components can be similar to or the same as any other switchable lens device described herein and their elements and components.

For example, the switchable lens system 100c can include controller 130c and input sensor 140c that can be similar to or the same as the controller 130 and input sensor 140 of the switchable lens device 110 (FIGS. 3A-3B). Moreover, the switchable lens system 100c can include an output device 150c. For example, as described above, the output device 150c can produce visually identifiable signals. For example, the output device 150c can be positioned near the eye 20, such that the signals from the output device 150c are visible to the eye 20. In an embodiment, the output device 150c can be positioned on or near the switchable lens 111c (e.g., the light emitted from the output device 150c can be at least partially transmitted through the switchable lens 111c). Hence, the signals from the output device 150c can be received by the subject.

In the illustrated embodiment, the controller 130c and input sensor 140c can be included in or mechanically connected to the frame 113c of the spectacles of the switchable lens system 100c. It should be appreciated, however, that the controller 130c, input sensor 140c, or output device 150c can be positioned on any portion of the switchable lens device 110c (e.g., on any portion of the frame 113c, on the switchable lens 111c, on the switchable lens 111c', etc.). Additionally or alternatively, the controller 130c, input sensor 140c, or output device 150c can be positioned externally to the switchable lens device 110c (e.g., the controller 130c, input sensor 140c, or output device 150c can be included in or attached to a device that can be configured to be carried by the subject, such as a smart phone).

Figure 7A:
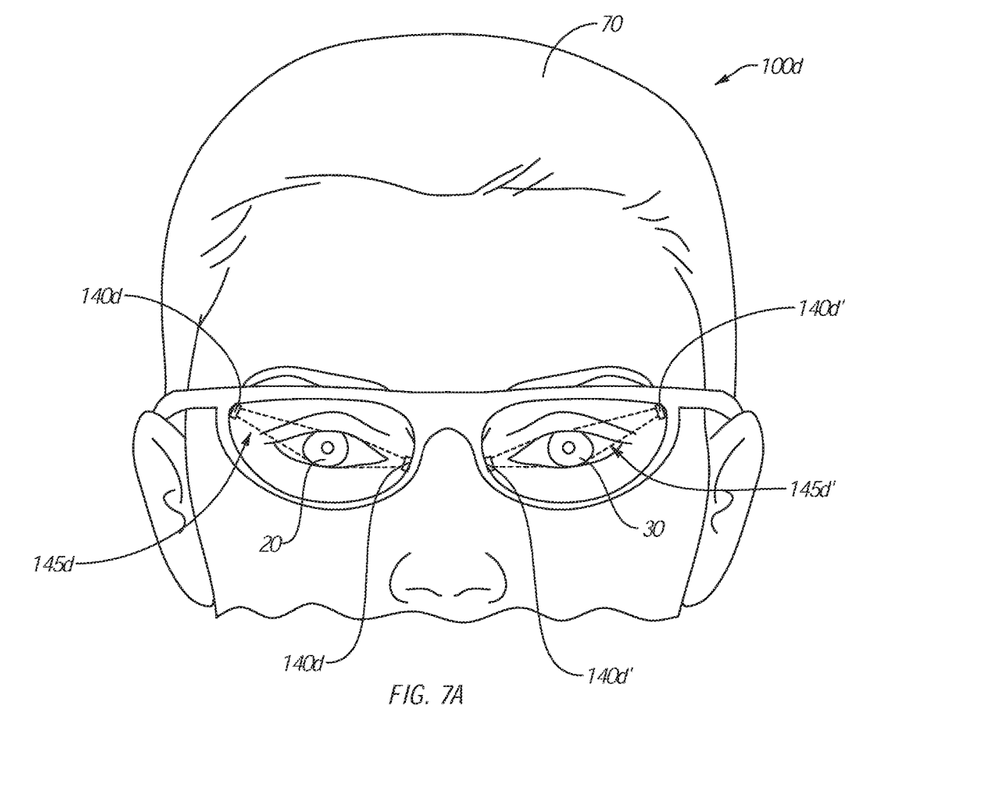
FIG. 7A is a schematic front view of a switchable lens system worn by a subject, according to an embodiment.
Figure 7B:
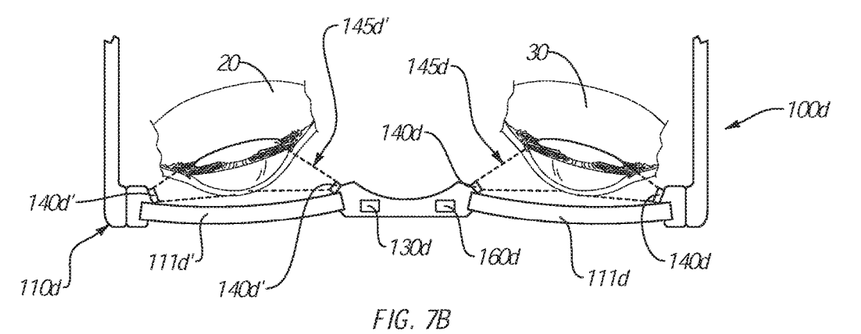
FIG. 7B is a schematic top view of the switchable lens system of FIG. 7A.

As described above, the switchable lens system or switchable lens device can receive one or more non-audible inputs, such as gestures from the subject. For example, the switchable lens system or switchable lens device can include one or more detectors configured to receive or detect gestures provided by the subject. FIGS. 7A-7B illustrate a switchable lens system 100d, according to an embodiment. Except as described there, the switchable lens system 100d and its elements and components can be similar to or the same as any of the switchable lens systems described herein and their corresponding elements and components.

In an embodiment, the switchable lens system 100d can include a switchable lens device 110d that is configured as spectacles. The switchable lens device 110d can include a controller 130d and communication device 160d that can be similar to or the same as the controller 130 and communication device 160 (FIGS. 3A-3B). In an embodiment, the switchable lens system 100d can include one or more input sensors 140d or one or more input sensors 140d'. For example, the input sensors 140d or input sensors 140d' can include or comprise one or more cameras configured to capture within their respective fields-of-view one or more portions of the body of the subject 70. For example, the cameras of the input sensors 140d can have a field-of-view 145d and the cameras of the input sensors 140d' can have a field-of-view 145d'. In an example, the field-of-view 145d can be suitably sized and configured to capture movement of the eye 20 and the field-of-view 145d' can be suitably sized and configured to capture movement of the eye 30.

In an embodiment, as described above, the controller 130d can be operably coupled to the input sensors 140d or to the input sensors 140d' and can receive signals therefrom. For example, signals received at the controller 130d from the input sensors 140d or input sensors 140d' can be related by the controller 130 to movement of one or more portions the eye 20 or eye 30 of the subject 70. Hence, for example, the controller 130*d* can be configured to distinguish movements of the eye 20 or of the eye 30 that correspond to one or more gesture commands for changing an optical setting of the switchable lens 111*d* or of the switchable lens 111*d'* from movements of the eye 20 or eye 30 that do not correspond to a gesture command for changing an optical setting.

In an embodiment, the fields-of-view 145*d* or 145*d'* can be configured such that the input sensors 140*d* or input sensors 140*d'*, respectively, can capture blinking of the eye 20 or eye 30. As mentioned above, a selected sequence of blinks of the eye 20 or of the eye 30 can correspond to a command for switching an optical setting of the switchable lens 111*d* or switchable lens 111*d'*. Hence, for example, the controller 130*d* can receive signals from the input sensors 140*d* or input sensors 140*d'* and can correlate the signals received from the input sensors 140*d* or input sensors 140*d'* to one or more commands for changing to a selected optical setting for the switchable lens 111*d* or switchable lens 111*d'*. In an embodiment, as described above, responsive to the signals received from the input sensors 140*d* or input sensors 140*d'*, the controller 130*d* can change optical setting of the switchable lens 111*d* or switchable lens 111*d'*. Additionally or alternatively, the selected movements of the eye 20 or eye 30 or movement patterns can correspond to a command for changing to a selected optical setting.

Figure 8:
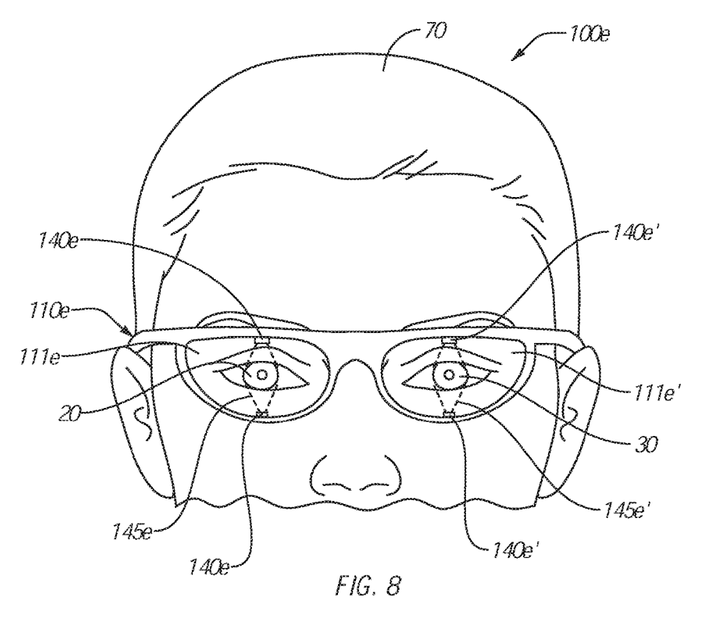
FIG. 8 is a schematic front view of a switchable lens system worn by a subject, according to an embodiment.

In an embodiment shown in FIGS. 7A-7B, the fields-of-view 145*d* and 145*d'* are oriented generally horizontally relative to the eyes 20, 30. It should be appreciated, however, that positions of the cameras of the input sensors 140*d*, 140*d'* and the orientation of the corresponding fields-of-view 145*d* and 145*d'* can vary from one embodiment to the next. FIG. 8 illustrates a switchable lens system 100*e*, according to an embodiment. Except as otherwise described herein, the switchable lens system 100*e* and its elements and components can be similar to or the same as any of the switchable lens systems described herein (e.g., similar to or the same as the switchable lens system 100*d* (FIGS. 7A-7B)).

In an embodiment, the switchable lens system 100*e* can include switchable lens device 110*e* that can have input sensors 140*e* and input sensors 140*e'* (e.g., as described above, the input sensors 140*e* and input sensors 140*e'* can include one or more cameras). In the illustrated embodiment, fields-of-view 145*e* and 145*e'*, of the corresponding input sensors 140*e*, 140*e'*, can be aligned generally vertically relative to the eye 20 and eye 30, respectively. For example, similar to the fields-of-view 145*d*, 145*d'* (FIGS. 6A-6B), the input sensors 140*e* or input sensors 140*e'* can capture movements of one or more portions of the eye 20 or eye 30 (respectively), which can correspond to one or more commands for switching switchable lens 111*e* or switchable lens 111*e'* to a selected optical setting.

Figure 9:
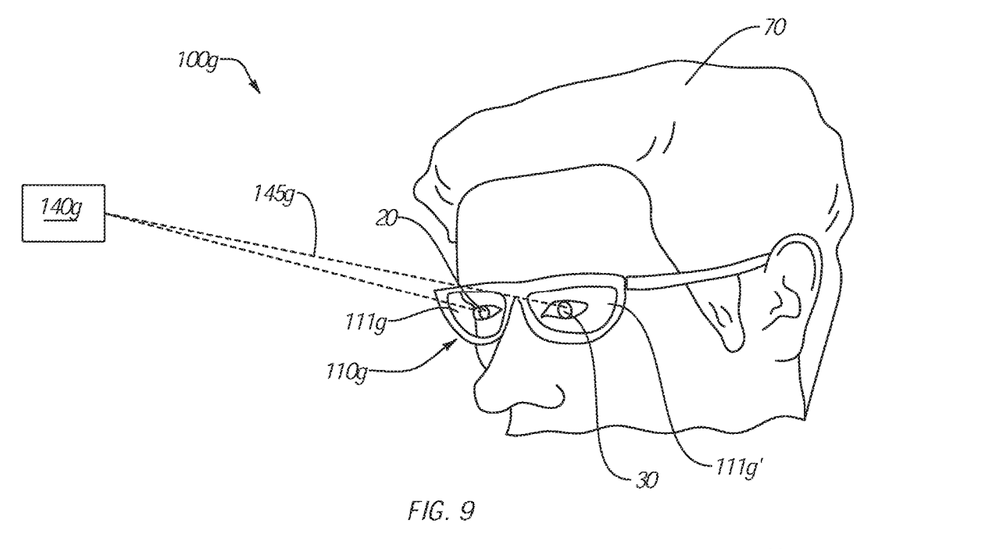
FIG. 9 is a schematic side view of a switchable lens system worn by a subject, according to an embodiment.

As mentioned above, the elements or components of the switchable lens system can be positioned externally to the switchable lens device. FIG. 9 illustrates a switchable lens system 100*g*, according to an embodiment. Except as described herein, the switchable lens system 100*g* and its elements and components can be similar to or the same as any of the switchable lens systems described herein. In the illustrated embodiment, the switchable lens system 100*g* can include switchable lens device 110*g* that includes switchable lens 111*g* and switchable lens 111*g'* that can be positioned in front of the eye 20 and eye 30, respectively.

In an embodiment, the switchable lens system 100*g* can include input sensor 140*g* that can be positioned externally to the switchable lens device 110*g*. For example, the input sensor 140*g* can include at least one camera that can be positionable such that the field-of-view 145*g* of the camera of the input sensor 140*g* can capture movement of one or more parts of the subject 70. For example, the field-of-view 145*g* can be suitable to capture movement of the eye 20 or eye 30 of the subject, of the subject's head, etc. As described above, for example, movement of the eye 20 or eye 30 of the subject can be received as one or more gesture commands or can be correlated to one or more commands for switching the switchable lens 111*g* or switchable lens 111*g'* to a selected optical setting. Moreover, in an embodiment, one or more additional or alternative movements of the subject 70 can be correlated with one or more selected optical settings (e.g., movement of the hand, arm, mouth, etc., can be correlated to a command for a selected optical setting). Hence, for example, the subject 70 can provide any number of suitable inputs to the controller via one or more selected movements, to select a suitable optical setting for the switchable lens 111*g* or switchable lens 111*g'*.

In an embodiment, the input sensor 140*g* can include one or more audio sensors (e.g., as described above). Hence, for example, the input sensor 140*g* can receive or detect one or more audio inputs from the subject 70 and can generate one or more signals responsive to the detected audible inputs from the subject 70. For example, as described above, the controller can receive one or more signals from the input sensor 140*g*, which can be related to the audible input provided by the subject 70, and can switch or direct switching of the switchable lens 111*g* or switchable lens 111*g'* at least in part based on the signals received from the input sensor 140*g*.

Generally, the input sensor 140*g* can be positioned at any suitable location (e.g., relative to the subject 70 or relative to the switchable lens device 110*g*). In an embodiment, the input sensor 140*g* can be positioned on or near a monitor, television, etc., in a manner that can facilitate detection or sensing of the inputs provided by the subject 70. Additionally or alternatively, the input sensors 140*g* can be operably coupled to or integrated with a device that can be carried by the subject 70 (e.g., in a smart phone).

Figure 10:
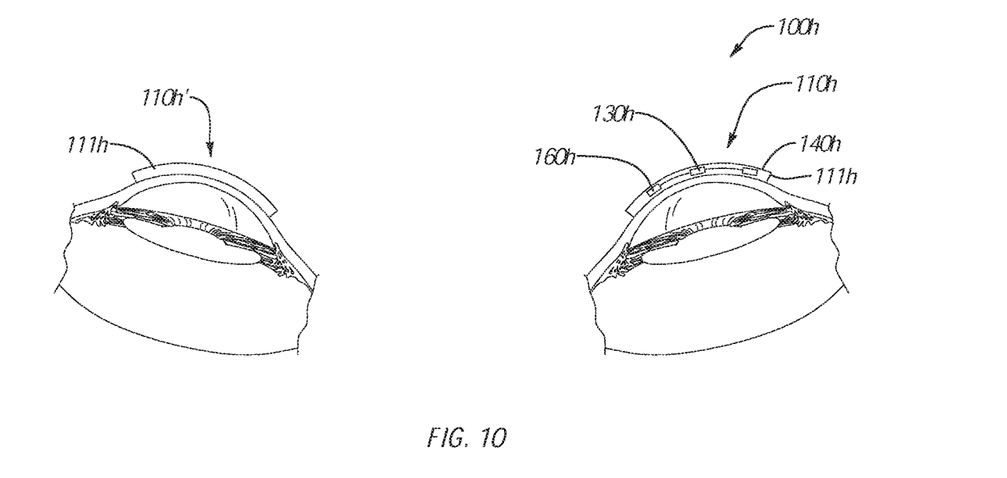
FIG. 10 is a schematic top view of the switchable lens system, according to an embodiment.

As discussed above, the switchable lens can be included in any number of suitable optical devices that can be used or worn by the subject. FIG. 10 is a top schematic view of a switchable lens system 100*h* that includes switchable lens devices 110*h*, 110*h'* configured as contact lenses and positioned on the respective eyes 20 and 39, according to an embodiment. Except as otherwise described herein, the switchable lens system 100*h* and its elements and components can be similar to or the same as any of the switchable lens systems described herein. For example, the switchable lens devices 110*h*, 110*h'* of the switchable lens system 100*h* can include corresponding switchable lenses 111*h* and 111*h'*.

In an embodiment, the switchable lens device 110*h* can include a controller 130*h*, an input sensor 140*h*, and a communication device 160*h*. For example, the input sensor 140*h* can be operably coupled to the controller 130*h* (e.g., as described above) and can receive or detect one or more inputs from the subject. In an embodiment, the input sensor 140*h* can include a microphone, one or more acceleration or motion detectors (e.g., accelerometers), an optical detector, combinations thereof, etc., which can detect one or more audible or gesture inputs or commands from the subject.

Moreover, the communication device 160*h* can send one or more signals to the switchable lens device 110*h'* (e.g., one or more switching signals). In an embodiment, the communication device 160*h* can be operably coupled to another controller or to an input/output interface of a controller (e.g., to a personal electronic device) and can receive signals therefor or send signals thereto. For example, the communication device 160h can receive one or more inputs from an external controller (e.g., from a personal electronic device on the subject) and, responsive thereto, can send one or more signals to the controller 130h. For example, personal electronic device of the subject can detect one or more gesture or audible inputs or commands provided by the subject and can send one or more signals to the communication device 160h responsive thereto. In an embodiment, as described above, the controller 130h can receive one or more signals from the communication device 160h (e.g., corresponding or responsive to the signals received from the external controller, such as personal electronic device) and can generate one or more switching signals from the switchable lens 111h or 111h'.

Figure 11:
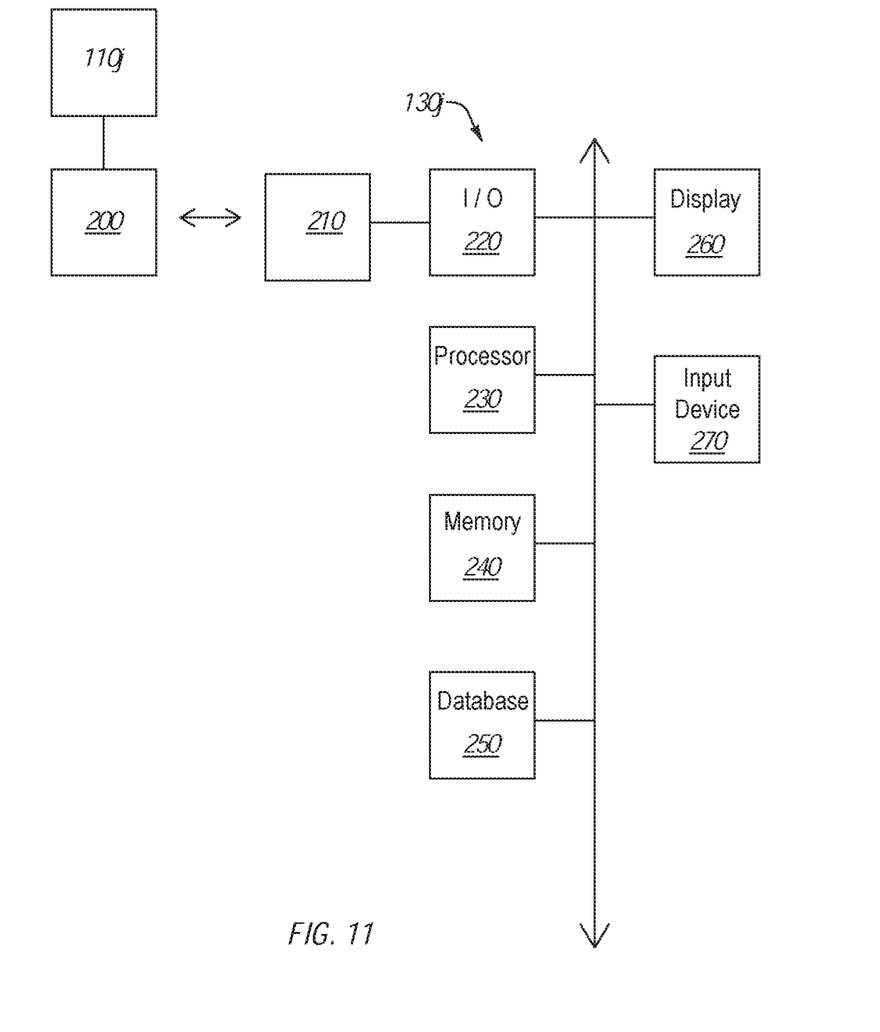
FIG. 11 is a schematic diagram of a switchable lens system, according to an embodiment.

FIG. 11 is a schematic diagram of a switchable lens system 100j that includes a switchable lens device 110j, according to an embodiment. In an embodiment, as shown in FIG. 11, the switchable lens device 110j can include or can be coupled to a communication device 200 (e.g., at least one receiver, transmitter, transceiver, or combinations thereof) that can receive data or instructions related to modification of the focal length(s) of one or more switchable lenses of the switchable lens device 110j. As described above, a switchable lens system can include the controller 130j (e.g., the controller 130j can receive one or more signals and can determine vergence rotation of the eye and/or suitable focal length for the switchable lenses of the switchable lens device 110j). In an embodiment, the controller 130j can include I/O interface 220, processor 230, and memory 240 operably coupled together. In an embodiment, the controller 130j can include a database 250 (e.g., the database 340 and can have data stored in a storage memory of the controller 130j). For example, the controller 130j can store one or more parameters in the database 340 (e.g., the controller 130j can store training or tuning data in the database 340).

In an embodiment, a communication device 210 (e.g., at least one receiver, transmitter, transceiver, or combinations thereof) can be operably coupled to the controller 130j and/or integrated therewith. For example, the communication device 210 can be operably coupled to the communication device 200 (e.g., via wired or wireless connection), such that the switchable lens device 110j and the controller 130e can transmit and receive data from one another. In an embodiment, display 260 and/or input device 270 (e.g., physical or virtual keyboard, microphone, etc.) can be operably coupled to the controller 130j and/or integrated therewith. For example, a user (e.g., a subject using and/or wearing the switchable lens device 110j) can enter input and/or data into the controller 130j, as described herein. Moreover, it should be appreciated that the controller 130j can be operably coupled to and/or incorporated with any number of suitable devices, such as personal electronic devices (e.g., personal computers, smart phones, tablets, etc.) and/or any other computing and/or input devices. It should be appreciated that any of the systems described herein (e.g., multi-focus lens systems, IOL systems, etc.) can have a similar or the same configuration as the system described above and illustrated in FIG. 11.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A lens system, comprising:
    at least one switchable lens device sized and configured to be placed in association with at least one of a first eye of a subject or a second eye of the subject, the at least one switchable lens device including at least one switchable lens having a plurality of optical settings and being configured to selectively switch at least between a first optical setting of the plurality of optical settings and a second optical setting of the plurality of optical settings;
    wherein the first optical setting includes at least one of a first focal spot or a first visible-light-transmittance setting of the at least one switchable lens;
    wherein the second optical setting includes at least one of a second focal spot or a second visible-light-transmittance setting of the at least one switchable lens; and
    a controller operably coupled to the at least one switchable lens device, the controller including control electrical circuitry configured to:
        receive one or more audible inputs from the subject;
        correlate the one or more received audible inputs with the first optical setting of the plurality of optical settings; and
        direct switching of the at least one switchable lens from the first optical setting of the plurality of optical settings to the second optical setting of the plurality of optical settings,
        wherein at least one of:

the controller is configured to filter out at least one of voice commands from persons other than the subject or non-command signals from the subject;

the one or more audible inputs include at least one of clapping, clicking, clacking of teeth, one or more words, one or more phrases, one or more numbers, or one or more parameters; or the one or more audible inputs include one or more of a series, sequence, or pattern of non-verbal commands or sounds.

2. The lens system of claim 1, wherein the first focal spot is offset laterally relative to the second focal spot.

3. The lens system of claim 2, wherein the first focal spot is offset horizontally relative to the second focal spot.

4. The lens system of claim 2, wherein the first focal spot is offset vertically relative to the second focal spot.

5. The lens system of claim 1, wherein on the first visible-light-transmittance setting, the at least one switchable lens allows a different amount of light of one or more wavelengths to pass therethrough than on the second visible-light-transmittance setting.

6. The lens system of claim 1, wherein the control electrical circuitry of the controller is configured to receive the one or more audible inputs that include an audible command.

7. The lens system of claim 6, wherein the audible command includes a voice command from the subject.

8. The lens system of claim 7, wherein the voice command includes one or more of the words or the phrases corresponding to at least one of a request for switching the at least one switchable lens from the first optical setting to the second optical setting or from the second optical setting to the first optical setting.

9. The lens system of claim 7, wherein the controller is configured to filter out the voice commands from the persons other than the subject.

10. The lens system of claim 6, wherein the audible command includes the non-verbal commands or sounds.

11. The lens system of claim 10, wherein the selected non-verbal commands or sounds includes the sound of at least one of the clapping, the clicking, or the clacking of teeth.

12. The lens system of claim 10, wherein the audible command includes the series, sequence, or pattern of non-verbal commands; the series, sequence, or pattern of the non-verbal commands or sounds includes the non-verbal commands or sounds repeated a selected number of times.

13. The lens system of claim 6, wherein the control electrical circuitry of the controller is operably coupled to an audio input device that is configured to generate one or more signals responsive to the audible command, and the control electrical circuitry of the controller is configured to correlate the one or more signals received from the audio input device with a request for switching the at least one switchable lens from the first optical setting to the second optical setting.

14. The lens system of claim 1, wherein the at least one switchable lens device includes a haptic and the at least one switchable lens is movable relative to the haptic.

15. The lens system of claim 14, wherein when the at least one switchable lens is on the first optical setting, the at least one switchable lens is positioned at a first position relative to the haptic, when the at least one switchable lens is on the second optical setting, the at least one switchable lens is positioned at a second position relative to the haptic, and the first position is different from the second position.

16. The lens system of claim 15, wherein the control electrical circuitry of the controller is configured to receive the one or more audible inputs that include an audible command.

17. The lens system of claim 16, wherein the audible command includes a voice command from the subject.

18. The lens system of claim 17, wherein the voice command includes one or more selected words or phrases corresponding to at least one of a request for switching the at least one switchable lens from the first optical setting to the second optical setting or from the second optical setting to the first optical setting.

19. The lens system of claim 16, wherein the control electrical circuitry of the controller is operably coupled to an audio input device that is configured to generate one or more signals responsive to the audible command, and the control electrical circuitry of the controller is configured to correlate the one or more signals received from the audio input device with a request for switching the at least one switchable lens from the first optical setting to the second optical setting or from the second optical setting to the first optical setting.

20. The lens system of claim 1, wherein the first focal spot is offset laterally relative to the second focal spot.

21. The lens system of claim 1, wherein the first focal spot is offset horizontally relative to the second focal spot.

22. The lens system of claim 1, wherein the first focal spot is offset vertically relative to the second focal spot.

23. The lens system of claim 1, further including an output device operably coupled to the control electrical circuitry of the controller and configured to output a confirmation of receiving the one or more inputs from the subject.

24. The lens system of claim 1, wherein the first optical setting includes a first focal length that is different from a second focal length of the second optical setting.

25. A lens system, comprising:
at least one switchable lens device sized and configured to be placed in association with at least one of a first eye of the subject or a second eye of the subject, the at least one switchable lens device including at least one switchable lens having a plurality of optical settings and being configured to selectively switch at least between a first optical setting of the plurality of optical settings and a second optical setting of the plurality of optical settings;

wherein the first optical setting includes at least one of a first focal spot or a first visible-light-transmittance setting of the at least one switchable lens;

wherein the second optical setting includes at least one of a second focal spot or a second visible-light-transmittance setting of the at least one switchable lens; and a controller operably coupled to the at least one switchable lens device, the controller including control electrical circuitry configured to:
receive one or more selected gesture inputs from the subject, the one or more selected gesture inputs include movement of the subject's head, movement of the subject's hand, movement of the subject's mouth, or blinking;
correlate the one or more received selected gesture inputs with the first optical setting of the plurality of optical settings; and
direct switching of the at least one switchable lens from the first optical setting of the plurality of optical settings to the second optical setting of the plurality of optical settings.

26. The lens system of claim 25, further including a sensor configured to detect the one or more selected gesture by the subject, the sensor being operably coupled to the control electrical circuitry of the controller.

27. The lens system of claim 26, wherein the sensor includes at least one of an accelerometer, a gyroscope, or a camera.

28. The lens system of claim 26, wherein the sensor is configured to be positioned in at least one of the first eye of the subject or the second eye of the subject.

29. The lens system of claim 26, wherein the sensor is configured to be positioned remotely from the first eye of the subject and the second eye of the subject.

30. The lens system of claim 29, wherein the sensor is included in a personal electronic device that is configured to be carried by the subject.

31. The lens system of claim 25, wherein the first focal spot is offset laterally relative to the second focal spot.

32. The lens system of claim 31, wherein the first focal spot is offset horizontally relative to the second focal spot.

33. The lens system of claim 31, wherein the first focal spot is offset vertically relative to the second focal spot.

34. The lens system of claim 25, wherein on the first visible-light-transmittance setting, the at least one switchable lens allows a different amount of light of one or more wavelengths to pass therethrough than on the second visible-light-transmittance setting.

35. The lens system of claim 25, wherein the at least one switchable lens device includes a haptic and the at least one switchable lens is movable relative to the haptic.

36. The lens system of claim 35, wherein when the at least one switchable lens is on the first optical setting, the at least one switchable lens is positioned at a first position relative to the haptic, when the at least one switchable lens is on the second optical setting, the at least one switchable lens is positioned at a second position relative to the haptic, and the first position is different from the second position.

37. The lens system of claim 25, further including a sensor configured to detect a selected gesture by the subject, the sensor being operably coupled to the control electrical circuitry of the controller.

38. The lens system of claim 25, wherein the control electrical circuitry of the controller is configured to receive the one or more inputs that include a detectable gesture by the subject, the detectable gesture being detectable by the sensor.

39. The lens system of claim 25, wherein the sensor includes at least one of an accelerometer, a gyroscope, or a camera.

40. The lens system of claim 25, wherein the sensor is configured to be positioned in at least one of the first eye of the subject or the second eye of the subject.

41. The lens system of claim 25, wherein the sensor is configured to be positioned remotely from the first eye of the subject and the second eye of the subject.

42. The lens system of claim 25, wherein the sensor is included in a personal electronic device that is configured to be carried by the subject.

43. The lens system of claim 25, further including an output device operably coupled to the control electrical circuitry of the controller and configured to output a confirmation of receiving the one or more inputs from the subject.

44. The lens system of claim 25, wherein the first optical setting includes a first focal length that is different from a second focal length of the second optical setting.

* * * * *